US00PP26117P3

(12) United States Plant Patent
Franken-Bembenek

(10) Patent No.: US PP26,117 P3
(45) Date of Patent: Nov. 24, 2015

(54) *PRUNUS* TREE ROOTSTOCK NAMED 'GI14813'

(50) Latin Name: ***Prunus* hybrid**
Varietal Denomination: Gi14813

(71) Applicant: Consortium Deutsche Baumschulen GmbH, Ellerbek (DE)

(72) Inventor: Sabine Franken-Bembenek, Giessen (DE)

(73) Assignee: Consortium Deutscher Baumschulen GmbH, Ellerbek (DE)

( * ) Notice: Subject to any disclaimer, the term of this patent is extended or adjusted under 35 U.S.C. 154(b) by 50 days.

(21) Appl. No.: 13/987,524

(22) Filed: Aug. 1, 2013

(65) Prior Publication Data

US 2015/0040275 P1 Feb. 5, 2015

(51) Int. Cl.
*A01H 5/08* (2006.01)
*A01H 5/00* (2006.01)

(52) U.S. Cl.
USPC ..... Plt./183
CPC ..... *A01H 5/00* (2013.01)

(58) Field of Classification Search
USPC ..... Plt./183
CPC ..... A01H 5/085
See application file for complete search history.

*Primary Examiner* — Keith Robinson
(74) *Attorney, Agent, or Firm* — The Webb Law Firm

(57) ABSTRACT

A new and distinct *Prunus* hybrid plant used as a rootstock for cherries that induces precosity and flat branching of the grafted plant.

4 Drawing Sheets

Botanical classification: *Prunus* hybrid.
Varietal denomination: 'Gi14813'.

BACKGROUND OF THE INVENTION

The present invention comprises a new and distinct cultivar of *Prunus* hybrid used as a rootstock known by the varietal name 'Gi14813'. The new variety was discovered in Giessen, Germany in 1971. The new variety is the result of a planned breeding program between *Prunus cerasus* 'Schattenmorelle' (unpatented female parent) and an unnamed *Prunus canescens* variety (unpatented male parent). The new variety differs from its parents in that it has a triploid genome, whereas the female parent has a tetrapoloid genome and the male parent has a diploid genome. The purpose of the breeding program was to produce a series of size-controlling, productive, and precocious rootstocks for sweet cherries. The new variety has been trial and field tested and has been found to retain its distinctive characteristics and remain true to type through successive propagations.

The new variety is similar to *prunus* rootstock 'GI 148/2' (U.S. Plant Pat. No. 9,622) in its rootstock induction of precosity, rootstock induction of flat branching, and the absence of root suckers. The color of the leaves of emerging branches in the Spring is more reddish (anthocyanin coloration) than 'GI 148/2'. Further, the vigor of a grafted tree on the new variety is greater than on 'GI 148/2'.

DESCRIPTION OF THE DRAWINGS

The accompanying photographic drawings illustrate the new cultivar, taken during the second vegetation period in a field in Kettig, Germany, with the color being as nearly true as is possible with color illustrations of this type.

DESCRIPTION OF THE PLANT

Figure 1:
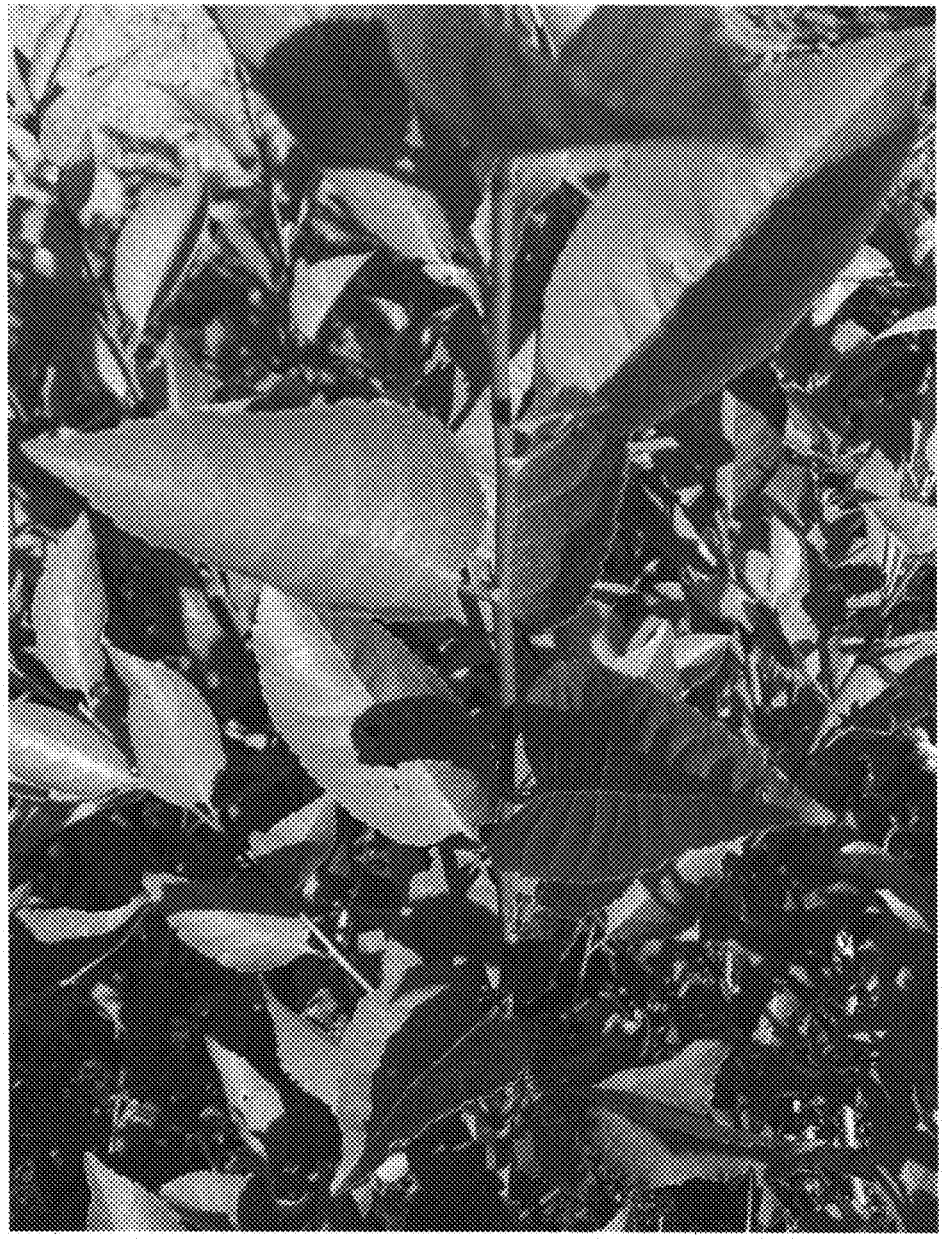
FIG. 1 is a close-up picture of the leaves and branches of the new variety.
Figure 2:
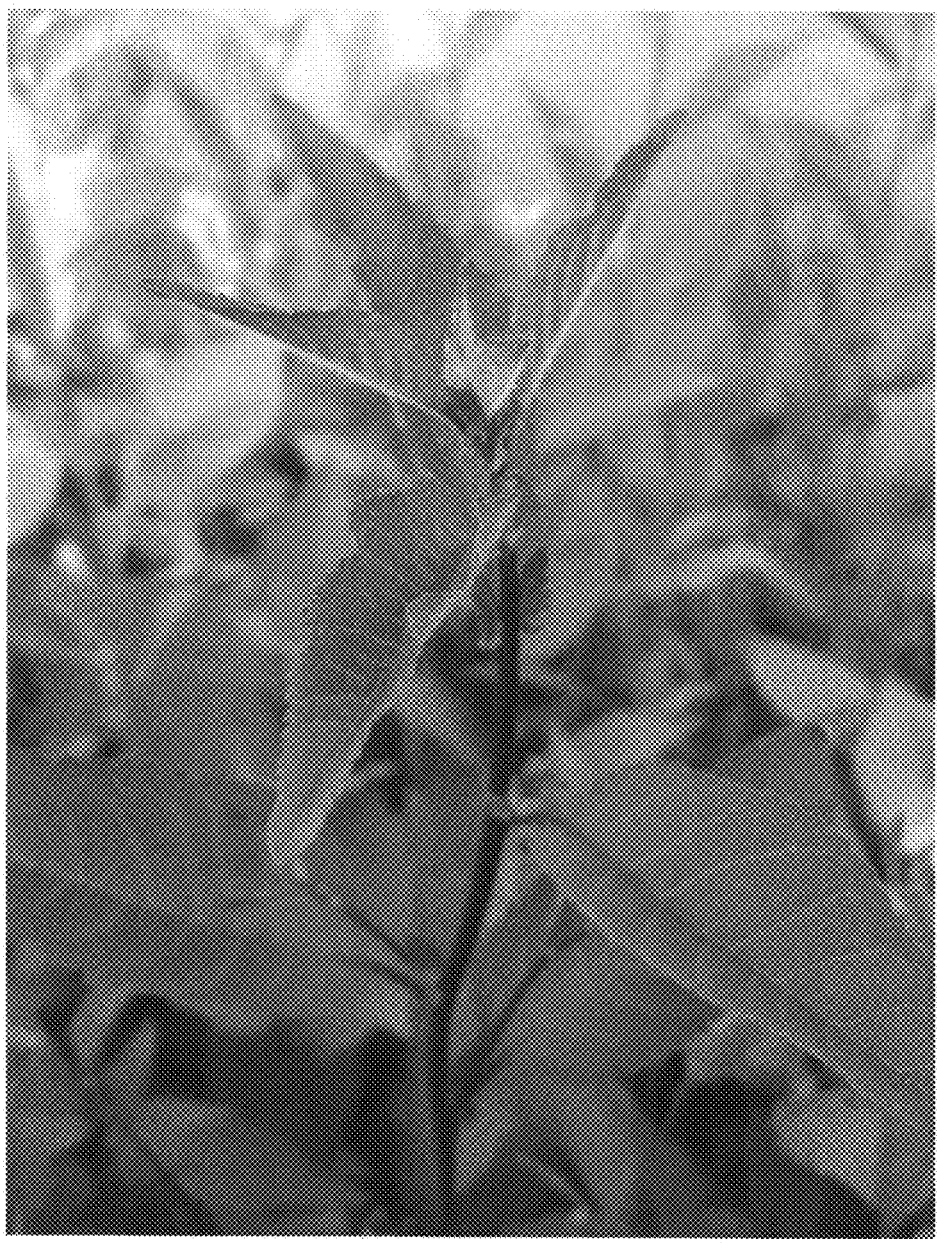
FIG. 2 is a close-up picture that shows both surfaces of the leaves of the new variety.
Figure 3:
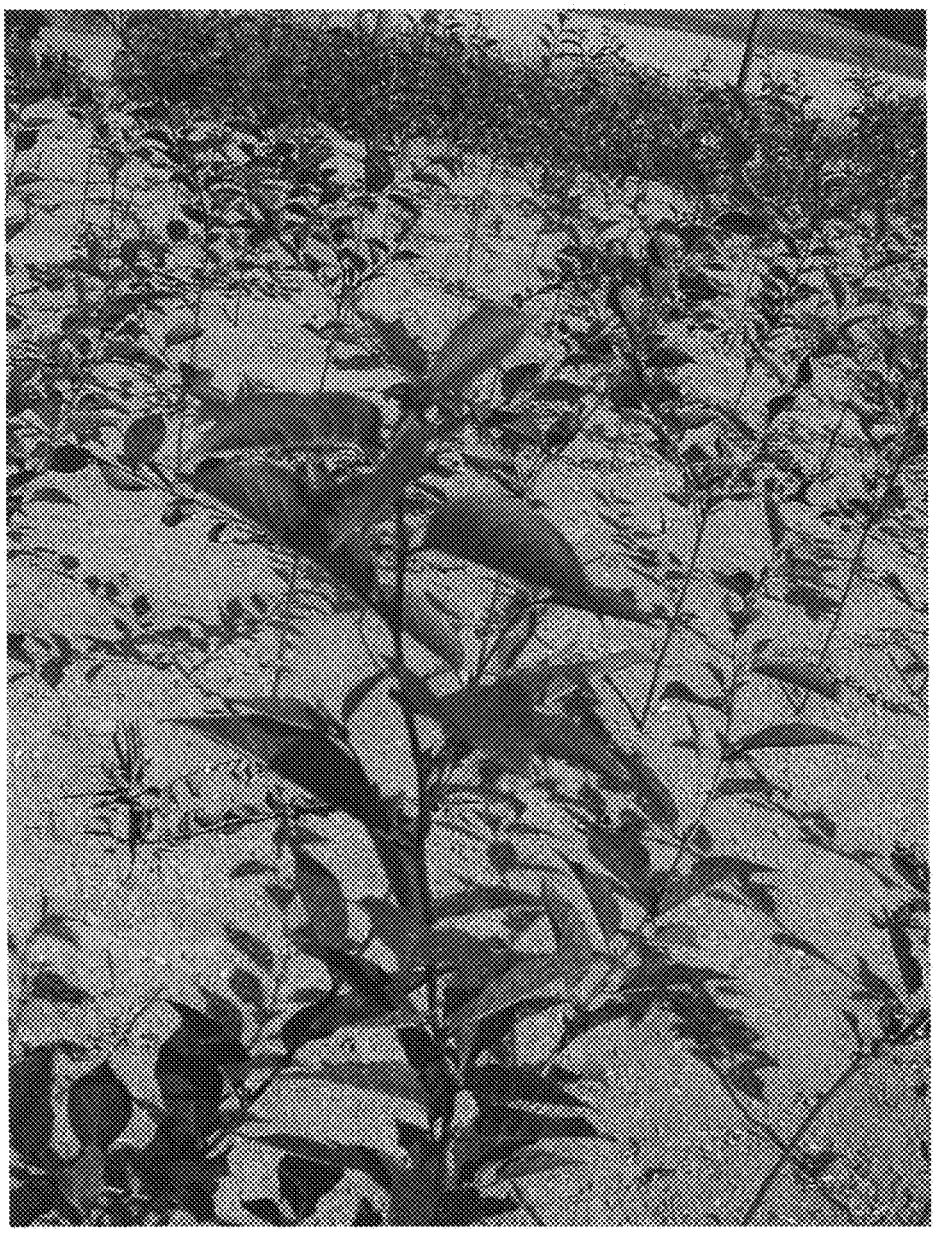
FIG. 3 is a picture of a field of plants of the new variety.
Figure 4:
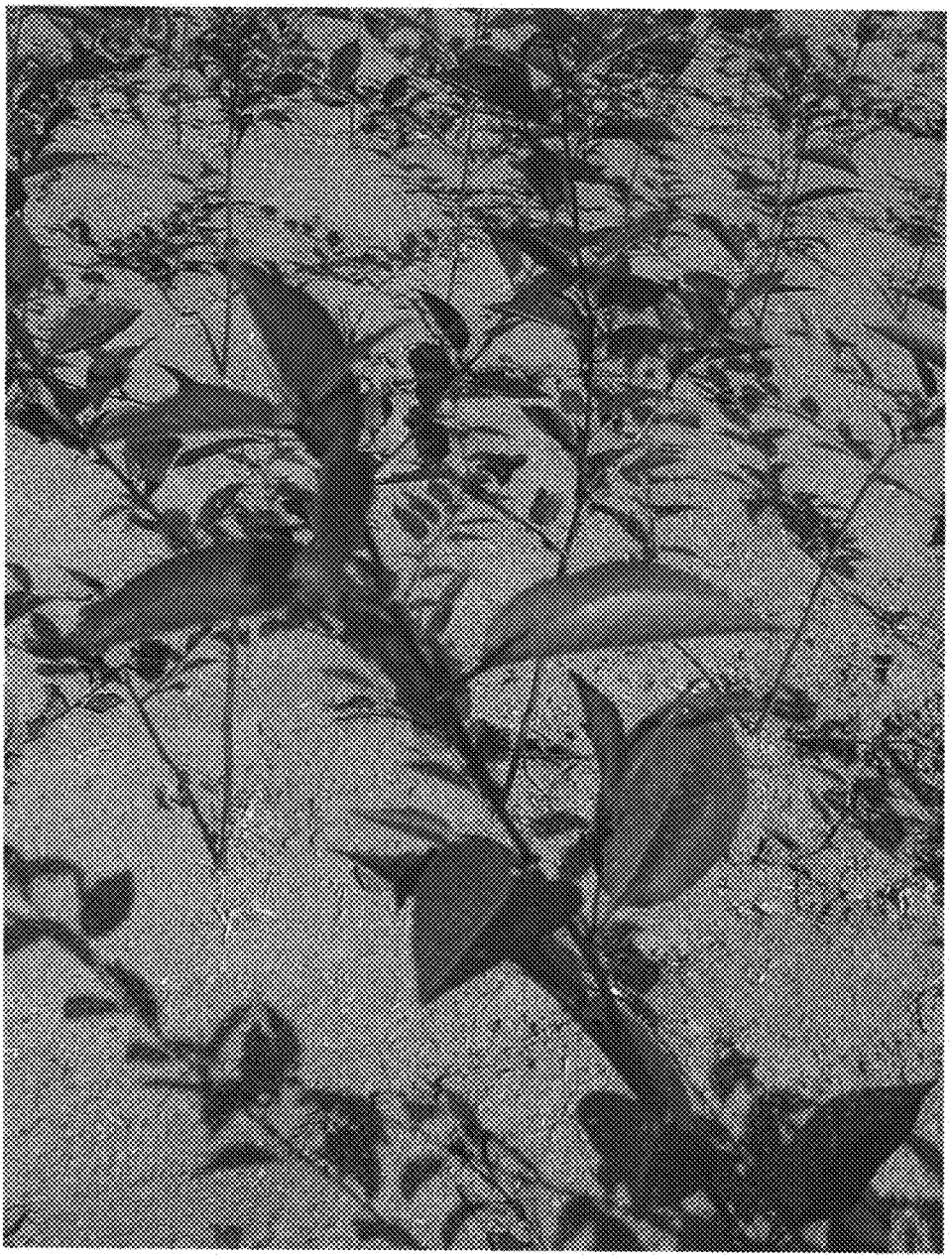
FIG. 4 is a further picture of a field of plants of the new variety.

The following detailed description sets forth the characteristics of the new cultivar. The data which defines these characteristics were collected by asexual reproduction carried by green cuttings under mist and in vitro conditions. The first asexual reproduction occurred in approximately 1975 in Giessen, Germany. The color readings were taken in natural daylight. Color references are primarily to The 2001 R.H.S. Colour Chart of The Royal Horticultural Society of London. Except where stated otherwise, the data collected for the description herein was taken on five-year old plants grown in an orchard under standard growing conditions in Witzenhausen-Wenderschausen, Germany.

PLANT

Use: As a rootstock for sweet, sour, and ornamental cherries.
Fragrance: None observed.
Growth type: Spreading to semi-upright.
Height: 215 cm five years after planting (in Giessen, Germany).
Spread: 140 cm five years after planting (in Giessen, Germany).
Trunk circumference: 50 mm two years after planting (in Giessen, Germany).
Branches:
*Internode length.*—Short.
*Diameter.*—Medium.
*Texture.*—Weak pubescence present.
*Color.*—144A.

Leaves:

*Length.*—Medium.

*Width.*—Medium.

*Form.*—Ovate.

*Apex.*—Acute.

*Base.*—Obtuse.

*Margin.*—Serrate.

*Upper surface texture.*—Medium glossy.

*Lower surface texture.*—Weak pubescence present.

*Venation pattern.*—Reticulate.

*Color.*—Upper surface: 137A. Lower surface: 137C.

*Petiole length.*—1.0 cm.

*Petiole texture.*—Weak pubescence present.

*Stipule length.*—Intermediate.

Flowers:

*Pedicel length.*—1.2 cm.

*Peduncle length.*—3.0 cm.

*Peduncle texture.*—Glabrous.

*Bud color.*—56D and 69C buds present at the popcorn stage.

*Bloom timing.*—Late, similar to the cultivar 'Regina' (not patented).

*Shape.*—Round.

*Petals.*—Number: Five. Length: 0.9 cm. Width: 0.9 cm. Shape: Round. Color (fully opened): White on both surfaces.

*Sepals.*—Number: Five. Length: 0.4 cm. Diameter: 0.4 cm. Color: 144A.

*Pistil number.*—One.

Tree winter hardiness: Good; USDA Hardiness Zone of 6 to 7 (possibly 5b to 8a).

Disease/pest/virus resistance or susceptibility: Some susceptibility observed to *Monilia laxa.*

Performance as a grafted rootstock:

*Root sprouts.*—No suckers observed.

*Anchorage.*—Good.

*Compatibility.*—Good.

*Vigor.*—Reduces size of tree to about 60% of a *Prunus avium* rootstock, comparable to the vigor of Gisela 6 and is somewhat more vigorous than Gisela 5.

I claim:

1. A new and distinct variety of *Prunus* hybrid plant used as rootstock as shown and described herein.

* * * * *